United States Patent [19]

Hellstrom et al.

[11] Patent Number: 5,055,559

[45] Date of Patent: Oct. 8, 1991

[54] ANTI-MELANOMA ANTIBODY MG-21 FOR DIAGNOSIS AND THERAPY OF HUMAN TUMORS

[75] Inventors: Karl E. Hellstrom; Ingegerd Hellstrom, both of Seattle, Wash.

[73] Assignee: Oncogen, Seattle, Wash.

[21] Appl. No.: 834,162

[22] Filed: Feb. 20, 1986

[51] Int. Cl.$^5$ ...................... A61K 35/16; C12N 15/06
[52] U.S. Cl. .............................. 530/387; 435/240.27; 435/188; 530/389; 530/390; 530/391; 424/85.91; 424/85.8; 424/1.1; 436/548
[58] Field of Search .................... 530/387; 435/240.27, 435/68; 436/548; 935/104, 107, 108, 110; 424/85

[56] References Cited

PUBLICATIONS

Hellstrom et al., 1985, Proc. Natl. Acad. Sci. 82:1499–1502.
Hellstrom et al., 1985, Monoclonal Antibodies and Cancer Therapy, (USCLA Symp. on Molec. and Cell. Biol., Alan R. Liss) pp. 149–164.
Hellstrom and Hellstrom in Accomplishments in Cancer Research 1985, 194:216–240 (J. F. Fortner, J. E. Rhoads, J. B. Lippincott. Co.).
Hellstrom et al., 1984, Contrib. to Oncol. Series: Genes and Antigens in Cancer Cells (Reithmuller, Koprowski, Van Kliest & Munk), pp. 121–131.
Dippold et al., 1983, Cancer Res., 44:806–901.
Burchell et al., in Monoclonal Antibodies for Tumor Detection and Drug Targeting (R. W. Baldwin & V. S. Byers, Acad. Press, 1985), pp. 1–15.
Hakomori, 1984, Ann. Rev. Immunol., 2:103–126.
Nepom, 1984, Proc. Natl. Acad. Sci., 81:2864–2867.
Koprowski et al., 1984, Proc. Natl. Acad. Sci., 81:216–219.
Hellstrom et al., 1983, J. Immunol., 130:1467–1472.
Nudelman et al., 1982, J. Biol. Chem., 257:12752–12756.
Brown et al., 1981, J. Immunol., 127:539–546.
Colcher et al., 1981, Cancer Res., 41:1451–1459.
Woodbury et al., 1980, Proc. Natl. Acad. Sci., 77:2183–2186.
Schulz et al., 1983, Proc. Natl. Acad. Sci., 80:5407–5411.
Fidler and Poste, 1982, Springer Semin. Immunopathol. 5:161–174.
Hellstrom et al., 1981, Int. J. Cancer, 27:281–285.
Uananue and Benacerraf, 1984, Text. Immunol. (Williams & Wilkins, Chapter (12)) pp. 218–238.
Julius et al., 1973, Eur. J. Immunol., 3:645–649.
Pollack et al., 1972, Int. J. Cancer, 9:316–323.
Skurzak et al., 1972, J. Exp. Med. 135:997–1002.
MacLennan et al., 1969, Immunol. 17:897–910.
Perlmann et al., 1969, Adv. Immunol. 11:117–193.
Hellstrom et al., 1965, Progr. Allergy 9:158–245.
Rowland et al., 1985, Cancer. Immunol. Immunother., 19:1–7.
DeNardo et al., 1985, Int. J. Radiation Oncology Biol. Phys., 11:335–348.
Kemshead in Monoclonal Antibodies for Tumor Detection and Drug Targeting (R. W. Baldwin & V. S. Byers, Academic Press, 1985) pp. 281–302.
Vitetta and Uhr, 1984, Transplant., 37:535–538.
Carrasquillo et al., 1984, Cancer Treatment Reports, 68:317–328.
Larson et al., 1983, J. Clin. Invest. 72:2101–2114.
Yeh et al., 1982, J. Cancer, 29:269–275.
Garrigues et al., 1982, Int. J. Cancer, 29:511–515.
Jansen et al., 1982, Immunol. Rev., 62:185–216.
Brown et al., 1981, Proc. Natl. Acad. Sci., 78:539–543.
Brown et al., 1979, J. Immunol. Meth., 31:201–209.
Hurwitz et al., 1975, Cancer Res., 35:1175–1181.
Cole et al., 1985, in Monoclonal Antibodies and Cancer Therapy (Alan R. Liss) pp. 77–96.
Takeda et al., 1985, Nature, 314:452–454.
Neuberger et al., 1984, Nature, 312:604–608.
Morrison et al., 1984, Proc. Natl. Acad. Sci., 81:6851–6855.
Cote et al., 1983, Proc. Natl. Acad. Sci., 80:2026–2030.
Pukel, C. S. et al., "$G_{D3}$, a Prominent Ganglioside of Human Melanoma, Detection and Characterization by Mouse Monoclonal Antibody", *J. Exp. Med.* 155: 1133–1147, Apr. 1982.
Dippold, W. G. et al. (I), "Inhibition of Human Melanoma Cell Growth in vitro by Monoclonal Anti-GD$_3$-Ganglioside Antibody", *Cancer Research* 44, 806–810, Feb. 1984.
Dippold, W. G. et al. (II), "Cell Surface Antigens of Human Malignant Melanoma: Definition of Six Antigenic Systems with Mounse Monoclonal Antibodies", *Proc. Nat'l Acad. Sci.* 77(10): 6114–6118, Oct. 1980.
Cheresh, D. A. et al., "Disialoganglioside GD3 on a Human Melanoma Serves as a Relevant Target Antigen for Monoclonal Antibody-Mediated Tumor Cytolysis", *Proc. Nat'l Acad. Sci.* 82: 5155–5159, Aug. 1985.
Ochi, A. et al., "Transfer of a Cloned Immunoglobulin Light-Chain Gene to Mutant Hydridoma Cells Restores Specific Antibody Production", *Nature* 302: 340–342, 1983.
Cerrottini et al., 1974, Adv. Immunol., 18:67–132.
Order, 1984, Comp. Ther. 10:9–18.
Ghose et al., 1972, Brit. Med. J., 3:495–499.
Ey et al., 1978, Immunochemistry, 15:429–436.
Kohler & Milstein, 1975, Nature, 256:495–497.

*Primary Examiner*—Garnette D. Draper
*Assistant Examiner*—Lila Feisee

[57] ABSTRACT

An antibody MG-21 which is directed against a tumor-associated glycolipid antigen and which is capable of activating serum complement or antibody dependent cellular cytoxicity is described. This antibody finds use in the therapy of cancers particularly melanoma and glioma. Proper administration of the antibody results in lysis of the tumor cells in vivo.

4 Claims, No Drawings

ANTI-MELANOMA ANTIBODY MG-21 FOR DIAGNOSIS AND THERAPY OF HUMAN TUMORS

1. Field of the Invention
2. Background of the Invention
   2.1. Tumor Cell Antigens and Anti-Tumor Antibodies
   2.2. Diagnostic Uses of Anti-Tumor Antibodies
   2.3. Therapeutic Uses of Anti-Tumor Antibodies as Carriers of Isotopes, Toxins or Drugs
3. Summary of the Invention
   3.1. Definitions
4. Detailed Description of the Invention
   4.1. The Antibody Molecules of the Invention
   4.2. Therapeutic Uses of Antibody MG-21
      4.2.1. Treatment of Melanoma
   4.3. Diagnostic uses of Antibody MG-21
5. Preparation of Monoclonal Antibodies
   5.1. Monoclonal Antibodies Directed Against Melanoma Glycolipids
6. Assays Used to Characterize the Monoclonal Antibodies
   6.1. Isotype Determination
   6.2. Antibody-Dependent Cellular Cytotoxicity Assay
      6.2.1. Isolation of Lymphocytes and Characterization of Effector Cells
      6.2.2. Treatment of Lymphocytes with With T-Cell Growth Factor
      6.2.3. Target Cells
   6.2. Complement Method Cytotoxicity Assay
7. Anti-Tumor Activity of Monoclonal Antibody MG-21
   7.1. Antibody Dependent Cellular Cytotoxicity Assay
   7.2. Complement-Mediated Cytotoxicity Assay
8. Deposit of Cell Lines

1. FIELD OF THE INVENTION

The present invention involves an antibody MG-21, that is (a) directed against a GD3 glycolipid antigen on the surface of tumor cells, particularly cells from melanomas and gliomas, and (b) capable of both activating complement and mediating an antibody-dependent cellular cytotoxicity resulting in the lysis of the tumor cells to which the antibody binds. The antibody of the present invention can be used in the diagnosis and treatment of tumors.

2. BACKGROUND OF THE INVENTION

2.1. TUMOR CELL ANTIGENS AND ANTI-TUMOR ANTIBODIES

Tumor cells express certain antigens which are absent from, or present in small amounts on, their normal cellular counterparts. Most of these are differentiation antigens, shared by the tumor and certain embryonic cells. Some of the antigens that appear with sufficient selectivity in tumors may serve as possible targets for therapeutic agents. This has been recently reviewed for malignant melanoma, which is one of the human tumors most studied in this respect (Hellstrom and Hellstrom, in Accomplishments in Cancer Research-194 Prize Year, General Motors Cancer Research Foundation, J. G. Fortner & J. E. Rhoads, eds., J. B. Lippincott Company, Philadelphia 1985, p 216–240), as well as for other tumors (Burchell and Taylor-Papadimitriou, in, R. W. Baldwin and V. S. Byers, eds., Monoclonal Antibodies for Tumor Detection and Drug Targeting, Academic Press, 1985, pp.1–15, Kemshead, ibid, pp. 281–302).

Many antibodies have been made to cell surface antigens that are expressed in greater quantities by human tumors than by normal tissues. It has also been well established that antibodies to cell surface antigens can be cytotoxic to tumor cells in the presence of complement (Hellstrom et al., 1962, Progr. Allergy 9: 158–245), and that some antibodies can mediate antibody-dependent cellular cytotoxicity, (Perlmann et al., 1969, Adv. Immunol. 11: 117–193; MacLennan et al., 1969, Immunol. 17: 897–910; Skurzak et al., 1972, J. Exp. Med. 135: 997–1002; Pollack et al., 1972, Int. J. Cancer, 9: 316–323). In the first case, an appropriate source of complement (generally rabbit or guinea pig), and in the latter case a source of effector cells (generally of mouse origin) is needed.

The evidence that antibodies to tumor-associated antigens can kill human tumor cells in the presence of human effector cells is more recent (Hellstrom et al., 1981, Int. J. Cancer 27: 281–285; as is the evidence that antibodies to such antigens can kill tumor cells in the presence of human serum as a source of complement (Hellstrom et al., 1985, Proc. Natl Acad Sci 82: 1499–1502; Hellstrom et al., 1985, Monoclonal Antibodies and Cancer Therapy, UCLA Symposia on Molecular and Cellular Biology, Vol. 27, pp.149–164 Alan R. Liss, Inc., N.Y.).

2.2. DIAGNOSTIC USES OF ANTI-TUMOR ANTIBODIES

Diagnostic uses of anti-tumor antibodies include immunohistology (Garrigues et al., Int. 1982, J. Cancer 29: 511–515) and immunocytology, as well as assays of serum for tumor products (Koprowski et al., 1981, Science 212: 53–55; Bast et al., 1983, New Engl. J. Med. 309: 883–887), and diagnostic imaging using labeled antibodies or antibody fragments (Larson et al., 1983, J. Clin. Invest. 72: 2101–2114)

2.3. THERAPEUTIC USES OF ANTI-TUMOR ANTIBODIES AS CARRIERS OF ISOTOPES, TOXINS OR DRUGS

Attractive approaches for preparing anti-cancer agents involve labeling antibodies with radioactive isotopes (Larson et al., 1983, J. Clin. Invest. 72: 2101–2114; Order, 1984, Compr. Ther. 10: 9–18; Carrasquillo et al., 1984, Cancer Treatment Reports 68: 317–328; de Nardo et al. 1985, Int. J. Radiation Oncology Biol. Phys. 11: 335–348), or conjugating antibodies to toxins (Jansen et al., 1982, Immunol. Rev. 62: 185–216; Vitetta and Uhr, 1984, Transplant. 37: 535–538) or anti-cancer drugs (Ghose et al., 1972, Brit. Med. J. 3: 495–499; Hurwitz et al., 1975, Cancer Res. 35: 1175–1181; Rowland et al., 1985, Cancer Immunol. Immunother. 19: 1–7). The antibody gives the specificity and the isotope or drug provides the ability to destroy the tumor. However, a disadvantage of this approach is the fact that both anti-cancer drugs and radioisotopes have a high level of toxicity to normal tissues. Thus, nonspecific uptake in various organs such as kidney, liver, or bone-marrow could lead to substantial side-effects.

3. SUMMARY OF THE INVENTION

The present invention is related to an antibody, MG-21, which is directed to GD3 glycolipid antigen at the surface of tumor cells and which belongs to a class of immunoglobulin, IgG3, capable of activating serum complement and/or mediating antibody dependent cellular cytotoxicity by human effector cells. The antibody of the present invention can lyse the tumor cells expressing the GD3 antigen both in vitro and in vivo.

The invention is also directed to methods for treating tumors in vivo using the antibody of the present invention as a therapeutic agent. After administration in vivo, the antibody of the present invention should bind preferentially to the tumor cells which express the glycolipid antigen. Upon binding to the tumor cell, either serum complement will be activated or antibody dependent cellular cytotoxicity will be mediated resulting in lysis of the tumor cells.

The antibody and method of the present invention offer several advantages over techniques which involve the use of antibody-conjugates, because radioisotopes and/or toxins, which may exhibit a high level of toxicity to normal tissues are not required. Moreover, nonspecific uptake of the unmodified antibody molecules of the present invention by normal tissues should result in minimizing side-effects of the therapy Furthermore, the antibody of the invention may be used in conjunction with other types of therapy, including chemotherapy and therapy with antibodies carring radioisotopes, toxins or drugs; antibody MG-21, by its ability to activate human complement, may increase the blood supply to tumor tissue and hence the concentration of bloodborne anti-tumor agents in the tumor.

3.1. DEFINITIONS

The terms listed below will have the meanings indicated:

ADCC=antibody dependent cellular cytotoxicity

4. DETAILED DESCRIPTION OF THE INVENTION

The present invention involves an antibody, MG-21, which is (a) directed against a tumor-associated GD3, glycolipid antigen, and (b) belongs to a subclass or isotype, IgG3, that is capable of mediating the lysis of tumor cells to which the antibody molecule binds. More specifically, this antibody belongs to a subclass or isotype that, upon complexing with the glycolipid tumor-associated antigen, activates serum complement and mediates antibody dependent cellular cytotoxicity (ADCC) by activating effector cells such as natural killer cells or macrophages.

The present invention is also directed to the use of this antibody, in its native form, for therapy of human tumors. Additionally, the antibody of the present invention could be used diagnostically in vivo or in vitro by attaching a label to the antibody molecule that can be detected. Such labels are well known in the art and include but are not limited to radioisotopes, radiolabels, radioopaque substances, enzymes or enzyme substrates, etc.

4.1. THE ANTIBODY MOLECULES OF THE INVENTION

Biological activity of antibodies is known to be determined, to a large extent, by the Fc region of the antibody molecule (Uanue and Benacerraf, 1984, Textbook of Immunology, 2nd Edition, Williams & Wilkins, Ch. 12 pp. 218-238). This includes their ability to activate complement and to mediate antibody-dependent cellular cytotoxicity (ADCC) as effected by natural killer cells or macrophages. Antibodies of different classes and subclasses differ in this respect. In general, antibodies of the IgG2a and IgG3 subclass and occasionally IgGl can mediate ADCC, and antibodies of the IgG3, IgG2a and IgM subclasses bind and activate serum complement. Complement activation generally requires the binding of at least two IgG molecules in close proximity on the target cell. However, the binding of only on IgM molecule activates serum complement.

The present invention concerns a mouse IgG3 antibody directed against a tumor cell surface glycolipid antigen which can mediate the killing of the human tumor cells in the presence of either human serum as a source of complement or human lymphocytes as a source of effector cells.

While the invention is demonstrated using a mouse monoclonal antibody, the invention is not so limited. Techniques recently developed for the production of "chimeric antibodies" (Morrison et al., 1984, Proc. Natl. Acad. Sci, 81: 6851-6855; Neuberger et al., 1984, Nature 312: 604-608; Takeda et al., 1985, Nature 314: 452-454.) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention, as long as the mouse part of the chimeric antibody molecule is derived from the gene coding for the variable region of antibody MG-21.

4.2 THERAPEUTIC USES OF ANTIBODY MG-21

The antibody of the present invention can be used in the therapy of cancers by administering the native antibody in an amount sufficient to cause reduction of the tumor by lysis of the tumor target cells whether the mechanism be complement activated lysis or ADCC.

There is evidence that complement activation in vivo leads to a variety of biological effects, including the induction of an inflammatory response and the activation of macrophages (Unanue and Benecerraf, 1984, Textbook of Immunology, 2nd Edition, Williams & Wilkins pp. 218-238). Tumor cells are more sensitive to a cytolytic effect of activated macrophages than are normal cells (Fidler and Poste, 1982, Springer Semin. Immunopathol. 5: 161-174). The increased vasodilation accompanying inflammation may increase the ability of various anti-cancer agents, such as chemotherapeutic drugs, radiolabeled antibodies etc., to localize in tumors. Therefore, antigen-antibody combinations of the type specified by this invention can be used therapeutically in many ways and may circumvent many of the problems normally caused by the heterogeneity of tumor cell populations (since antigen negative cells can also be killed using the approach of this invention). Additionally, anti-idiotypic antibodies (Nepom et al., 1985, Proc. Natl. Acad. Sci. 81: 2864-2867; Koprowski et al., 1984, Proc. Natl. Acad. Sci 81: 216-219) relating to the GD3 antigen defined by antibody MG-21 could be used to induce an active immune response in human cancer patients. Such a response includes the formation of antibodies capable of activating human complement and mediating ADCC and by such mechanisms cause tumor destruction.

In the examples of the present invention an IgG3 antibody, MG-21, which is specific for a GD3 ganglioside antigen expressed by cells from human melanoma can kill cells from the respective tumors in a short-term (2 or 4 hour $^{51}$Cr assay), if either complement is provided in the form of human serum or effector cells are provided in the form of human blood lymphocytes. Antibodies to either of two melanoma-associated protein antigens, p97 and a proteoglycan, which are expressed on the cells used as targets with anti-GD3 antibodies failed to produce either ADCC or complement dependent cytotoxic reactions. Serum from patients with cancer, even with disseminated cancer, could serve as a source of complement. Lymphocytes from patients with metastatic cancer did not mediate ADCC, but could be made to do so by exposure to T-cell growth factor.

4.2.1. TREATMENT OF MELANOMA

An IgG3 antibody, MG-21 is described that binds strongly to a human melanoma-associated GD3 antigen. It mediates ADCC when combined with human effector cells, and it kills melanoma cells in the presence of human serum as a source of complement.

High cytolytic activity was detected after 2 hours in $^{51}$Cr-release assays when human lymphocytes were combined with antibody and tested against cells expressing large amounts of the GD3 antigen; lymphocytes or antibodies alone were ineffective. Significant ADCC could be seen even at an antibody doses of 10 ng/ml and with one lymphocyte per target cell. The ADCC effect was antigen-specific, since cells lacking the GD3 antigen were not killed and the effect could be competitively inhibited by addition of antigen-positive tumor cells.

Antibody MG-21 is described in Hellstrom et al., 1985, Proc. Natl. Acad. Sci. USA 82: 1499–1502 which is incorporated herein by reference; in addition other IgG3 antibodies 2B2 and IF4 are described which have partially similar (but not identical) effects (they do not activate human complement). Antibody MG-21 is also described in copending U.S. application filed concurrently herewith, having Ser. No. 06/831684 filed Feb. 21, 1986 which is also herein by reference.

4.3. DIAGNOSTIC USES OF ANTIBODY MG-21

The antibody of the present invention can be used in the diagnosis and detection of GD3 positive tumors such as melanomas and gliomas. Accordingly, antibody MG-21 can be used in diagnostic techniques which are well known in the art such as immunohistological assays, immunocytological assays, serum assays and/or in diagnostic imaging procedures using antibody MG-21 labeled with an appropriate signal generating compound such as radioisotopes, radio-opaque compounds, fluorescent compounds, enzymes and/or enzyme substrates, dyes, and the like, in order to detect the presence or absence of GD3 positive tumor cells in a patient sample such as a biopsy, cell wash, body fluid, serum, etc.

5. PREPARATION OF MONOCLONAL ANTIBODIES

The subsections below describe how the antibodies used in the examples which follow were prepared.

The binding assays used to characterize the specificity of the antibodies were performed by using radiolabeled antibodies (Brown et al., 1981, Proc. Natl. Acad. Sci. 78: 539–543); cultured cells ($10^6$) were incubated at 4° C. for 30 minutes with $10^6$ cpm o: $^{125}$I-labelled antibody in 100 µl of heat-inactivated (30 minutes at 56° C.) fetal calf serum in culture medium. After the addition of 5 ml of PBS, the cells were pelleted by centrifugation for 10 minutes at 250×g. The supernatant was aspirated and the pellet was assayed for $^{125}$I. To measure nonspecific binding, parallel incubations were performed with 10 µg of unlabeled antibody as a competitor (Brown et al., 1981, Proc. Natl. Acad. Sci. 78: 539–543). In some instances binding assays were carried, out in an analogous fashion on cell monolayers attached to plastic culture dishes.

5 1. MONOCLONAL ANTIBODIES DIRECTED AGAINST MELANOMA GLYCOLIPIDS

In order to prepare antibodies directed against tumor-associated glycolipid antigens of melanoma cells, BALB/c mice were immunized with a melanoma cell line, SK-MEL-28, and their spleen cells subsequently were hybridized with NS-1 cells. Hybridoma supernatants were screened for binding to GD3 that had been isolated from melanoma tissue and attached to the surface of the wells of Falcon 3034 Microtest plates as previously described (Yeh et al., 1982, Int. J. Cancer 29: 269–275); irrelevant gangliosides were included as controls. Hybridoma MG-21 resulted from one of the hybridizations. It was cloned twice by limiting dilution. MG-21 makes an antibody that is IgG3 according to gel diffusion.

For comparison, two different antibodies, 96.5 and 48.7, were used. The former is an IgG2a antibody directed against p97, a melanoma associated glycoprotein of $M_r97,000$ (Woodbury et al., 1980, Proc. Natl. Acad. Sci. USA 77: 2183–2186; Brown et al., 1981, J. Immunol. 127: 539–546), and the latter is an IgG2b antibody specific for a proteoglycan antigen expressed by most melanomas (Hellstrom et al., 1983, J. Immunol. 130: 1467–1472). These antibodies have not, in previous experiments, given significant ADCC or inhibition of human melanomas in nude mice.

Antibodies were affinity-purified on a column of staphylococcal protein A covalently linked to Sepharose CL-4B (Pharmacia) by elution with 0.1 M citrate buffer, pH 3.5 or 4.5 (Brown et al., 1981, J. Immunol. 127: 539–546).

Antibody specificity for melanoma was established by binding assays with cultured cells, as published for antibody 4.2. (Yeh et al., 1982, Int. J. Cancer 29: 269–275; Nudelman et al., 1982, J. Biol. Chem. 257: 12752–12756). Specificity was confirmed by immunohistological studies on frozen section (Garrigues et al., 1982, Int. J. Cancer 29: 511–515), in which antibody MG-21 stained samples from approximately 80% of metastatic melanomas and appropriately 60% of gliomas, whereas normal tissues, including kidney and brain, were not stained; the specificity data for an antibody, 2B2, which is directed against the same GD3 antigen as MG-21, have been published (Hellstrom et al., 1984, Contributions to Oncology Series: Genes and Antigens in Cancer Cells, eds. Riethmuller, G., Koprowski, H., Van Kleist S. & Munk, K. (Karger, Basel), pp. 121–131.

6 ASSAYS USED TO CHARACTERIZE THE MONOCLONAL ANTIBODIES

6.1. ISOTYPE DETERMINATION

Two techniques were used to determine isotypes, Ouchterlony immuno-diffusion and an assay carried out in 96-well plates.

For Ouchterlony immunodiffusion, an aliquot of supernatant of particular hybridoma cells was placed into the center well of a 2% agar plate. Mono-specific rabbit anti-mouse Ig isotypes antibodies (Meloy Lab, Springfield, VI) were placed in the outer wells and plate was incubated for 2 hours at room temperature and overnight at 4° C.

Flexible polyvinylchloride 96 well plates (Costar) were coated with 0.1 mg/ml goat anti-mouse Ig antibodies for 2 hours at 37° C. and countercoated with a 3% BSA solution for 2 hours at 37° C. The hybridoma supernatant was then incubated at 37° C. for 2 hours. After washing with PBS, bovine serum albumin (BSA) plates were incubated at 37° C. for 2 hours with monospecific rabbit anti-mouse Ig isotype antibodies coupled to peroxidase (Zymed, South San Francisco, Calif.). After washing, plates were incubated with 1 mg/ml orthophenylenediamine and 0.03% $H_2O_2$ in 0.1 M citrate buffer pH 4.5. Optical density at a wavelength of 630 nm was determined on a Dynatec ELISA plate reader.

6.2. ANTIBODY-DEPENDENT CELLULAR CYTOTOXICITY ASSAY

A short-term $^{51}$Cr-release test was used to detect ADCC of target tumor cells (Cerrotini et al., 1974, Adv. Immunol. 8: 67-132). Peripheral blood lymphocytes from five healthy human subjects were separated on Ficoll-Hypaque (Hellstrom et al , 1981, Int. J. Cancer 27: 281-285) to provide effector cells and were prescreened for low (less than or equal to 5%) natural killer cell reactivity against SK-MEL-28 cells; unless indicated otherwise the ratio of lymphocytes to target cells was 100:1. Spleen lymphocytes from normal BALB/c mice were also included in two tests. Target cells ($10^6$) were labeled by incubation with 100 $\mu$Ci(1 Ci=37 GBq) of $^{51}$Cr for 2 hours at 37° C., after which they were washed three times and resuspended in medium. The labeled cells were seeded ($2\times10^4$ cells per well in 20 $\mu$l ) into Microtiter V-bottom plates (catalog no. 1-220-25X, Dynatech Laboratories, Alexandria, Vir.). Purified antibody (100 $\mu$l per well) then was added, followed by $2\times10^5$ lymphocytes per well in 100 $\mu$l; experiments with lower numbers of lymphocytes per well and with lower antibody concentrations also were carried out. The mixtures were incubated for 2 or 4 hours (See Tables and text), after which the plates were centrifuged at 400$\times$g. The supernatants were removed and the radioactivity in 100 $\mu$l samples was measured with a $\gamma$-counter. There were two replicates per group; the variation between replicates was always less than 10%. Spontaneous release was defined as the cpm released into the medium from target cells that were osmotically lysed at the end of the assay. Percent cytotoxicity was calculated as $$\frac{\text{experimental group release} - \text{spontaneous release}}{\text{total release} - \text{spontaneous release}} \times 100$$

6.2.1. ISOLATION OF LYMPHOCYTES AND CHARACTERIZATION OF EFFECTOR CELLS

Two types of donors of human blood lymphocytes and sera were tested. First, we used healthy, adult human subjects, 25–45 years of age. Second, we tested patients with melanoma. After the blood samples were drawn using 20 units heparin/ml of blood, lymphocytes were separated on Ficoll-Hypaque (Hellstrom et al., 1981, Int. J. Cancer 27: 281-285).

Most tests were done on lymphocytes frozen in a mixture of 10% dimethylsulfoxide (DMSO), 20% fetal calf serum and RPMI culture medium (Grand Island Biological Company, Grand Island, N.Y.) as previously described (Hellstrom et al., 1981, Int. J. Cancer 27: 281-285) and were thawed at 37° C. prior to testing.

In order to characterize the effector cells, tests were performed in which lymphocyte preparations obtained by separation on Ficoll-Hypaque were incubated for 1 hour at 37° C. in plastic culture flasks to remove adherent cells, after which they were passed through a nylon wool column (Julius et al., 1973, Eur. J. Immunol. 3: 645-649); the cells in the column effluents were used as a source of effector cells. In other tests, the Ficoll-Hypaque-purified lymphocytes were incubated for 1 hour at 37° C. with a mixture of anti-Leu-llb antibody (Becton-Dickinson, Mt. View, Calif.) at a concentration of 0.1 $\mu$g/$10^6$ lymphocytes and rabbit serum diluted 1:5 (as a source of complement); this was done in order to abolish reactivity mediated by natural killer (NK) cells (Thompson et al., 1982, American Association for Clinical Histocomp. Testing, 8th Annual Meeting, p. A23).

6.2.2. TREATMENT OF LYMPHOCYTES WITH T-CELL GROWTH FACTOR

Peripheral blood lymphocytes ($10^6$/ ml) were treated with T-cell growth-factor by incubating the lymphocytes in vitro for 5 days in the presence of 10% human T-cell growth factor (TGF, Cellular Products, Inc., Buffalo, N.Y.) 20% human AB serum and 70% RPMI culture medium.

6.2.3. TARGET CELLS

Five different human melanoma lines from metastatic melanoma were used. All except one, M-2634, express high levels of the GD3 antigen according to binding assays, which were carried out as previously described (Yeh et al., 1982, Int. J. Cancer 29: 269-275; Nudelman et al., 1982, J. Biol. Chem. 257: 12752-1-2756) Four of the lines, SK-MEL-28 (Woodbury et al., 1980, Proc. Natl. Acad. Sci. USA 77, 2183-2186), M-2669 clone 13, M-2634, and M-2765, were propagated in vitro. The fifth line, M-2586, failed to grow in vitro and so was serially transplanted in nude mice, were it grew better than any of the other lines. Human lung (bronchial) carcinoma line CH27 was used as a control for antibody specificity. It does not express detectable GD3 antigen.

6.3. COMPLEMENT MEDIATED CYTOTOXICITY ASSAY

The $^{51}$Cr-release assay also was used to test the ability of antibodies to kill melanoma cells in the presence of human serum as a source of complement. It was carried out similarly to the assays for ADCC, except that 100 $\mu$l of undiluted unheated human serum was added per microtest well, instead of a suspension of effector cells; this serum was derived from normal human subjects.

7. ANTI-TUMOR ACTIVITY OF MONOCLONAL ANTIBODY MG-21

The following subsections describe the results of various assays which demonstrate the ability of antibody MG-21 to induce ADCC and/or complement mediated killing of melanoma cells.

7.1. ANTIBODY DEPENDENT CELLULAR CYTOTOXICITY ASSAY

In the first set of experiments the M-2669 cell line, which are human melanoma cells expressing more than 100,000 molecules per cell of GD3 ganglioside antigen, were incubated with purified MG-21 and peripheral blood lymphocytes from a normal human subject. The data presented in Table I indicate that significant killing of the melanoma target cells was observed. In fact, significant killing of the melanoma target cells was observed even at a small antibody concentration (1 μg/ml) and a low lymphocyte to target cell ratio (10:1). By contrast, lymphocytes alone, the MG-21 antibody alone, or lymphocytes incubated with either antibody 96.5 which is directed against p97, a tumor-associated protein antigen, and antibody 48.7 directed against a proteoglycan also expressed strongly by the same melanoma cells, did not cause significant release of isotope.

TABLE I

ADCC against M-2669 Melanoma Cells as Targets and Human Lymphocytes Combined with Antibody MG-21 or Control Antibodies 96.5 and 48.7

| RATIO Human Lymphocytes Per Target Cell | % Cytotoxicity of M-2669 Target Cells | | |
|---|---|---|---|
| | MG-21 (μg/ml) 10 | MG-21 (μg/ml) 1 | 96.5 (μg/ml) 10 | 48.7 (μg/ml) 10 |
| 100 | 82 | 76 | 0 | 0 |
| 10 | 64 | 52 | ND | ND |
| 1 | 14 | 13 | ND | ND |

Cytotoxicity was determined in 4-hr $^{51}$Cr-release assay. Antibodies alone gave no cytotoxicity and lymphocytes alone gave less than or equal to 5% cytotoxicity. ND, not done.

The results in Table II show that incubation of the lymphocytes from normal subjects with anti-Leu-11b antibody and complement abolished the ability of the lymphocytes to lyse the target cells (i.e., to mediate ADCC) in the presence of MG-21. This indicates that the lymphocytes had the characteristics of natural killer (NK) cells (Thompson et al., 1982, Am. Assoc. for Clinical Histocompatibility Testing, 8th Annual Meeting, p. A23).

TABLE II

Inhibition of ADCC against M-2669 Melanoma Cells by Incubation of Lymphocytes from a Normal Subject with Anti-Leu-11b Antibody and Complement

| Treatment of Lymphocytes | % Cytolysis * | |
|---|---|---|
| | Lymphocytes Alone | Lymphocytes + MG-21 10 μg/ml |
| None (culture medium) | 3 | 24 |
| Complement | 3 | 22 |
| Anti-Leu-11b and Complement | 2 | 2 |

* 10 lymphocytes per target cell.

In view of the interest in developing therapy for human cancer, the next step was to investigate whether lymphocytes from patients with disseminated metastases could serve as effector cells in the ADCC assays, since these patients would most likely be the first candidates for therapeutic trials. As shown in Table III, lymphocytes from such patients failed to mediate significant ADCC. However, significant killing by lymphocytes along and an even greater killing by lymphocytes and MG-21 antibody was observed, if the lymphocytes were first incubates with a preparation containing a T-cell growth factor for 5 days; see Table IV.

TABLE III

ADCC against M-2669 Melanoma Cells and Lymphocytes from Normal Subjects or Melanoma Patients Combined With Antibody MG-21

| Human Lymphocyte Donor | % Cytotoxicity of M-2669 Target Cells | |
|---|---|---|
| | No Antibody | MG-21 |
| Normal Subjects | | |
| N-1 | 6 | 51 |
| N-3 | 6 | 55 |
| Stage IV Melanoma | | |
| M-3 | 4 | 2 |
| M-5 | 3 | 7 |
| Stage I Melanoma | | |
| M-2 | 0 | 31 |

100 effector cells (lymphocytes)/target cell (M-2669) and 50 μg/ml MG-21.

TABLE IV

NK Activity and ADCC against M-2669 Melanoma Cells and by Lymphocytes Incubated In Vitro with T-Cell Growth Factor (IL-2) for 5 Days Prior to Combining them with Antibody MG-21 and Target Cells

| Lymphocytes Donor | Ratio to Target Cell | MG-21 (μg/ml) | % Cytotoxicity of M-2669 Target Cells | |
|---|---|---|---|---|
| | | | Lymphocytes Un-Treated | Lymphocytes TCGF* Treated |
| Stage IV Prostate Carcinoma | 10 | 0 | 0 | 20 |
| | | 10 | 6 | 36 |
| Stage II Breast Carcinoma | 10 | 0 | 2 | 68 |
| | | 10 | 25 | 85 |
| | 1 | 0 | 2 | 29 |
| | | 10 | 11 | 55 |

7.2. COMPLEMENT-MEDIATED CYTOTOXICITY ASSAY

The cytotoxicity of antibody MG-21 to GD3-positive melanoma cells in the presence of human serum as a source of complement was determined using a 4-hr $^{51}$Cr-release assay similar to the ADCC assay by adding undiluted unheated human serum instead of lymphocytes. As shown in Tables V and VI antibody MG-21 gave a strong cytotoxice effect in the presence of huamn serum. Heat inactivation (56° C. for 30 minutes) of the human serum abolished this effect.

The results in Table V demonstrate that up to 100% of the target cells were lysed when antibody MG-21 and human serum were both added. Antibody MG-21 along and human serum along had no cytolytic effect on the melanoma cell, and inactivating the complement abolished the cytolytic effect.

TABLE V

Lysis of Tumor Cells by Antibody MG-21 In the Presence of Unheated Human Serum as a Source of Complement

| Target Cells | GD3 Expression | Complement | MG-21 (μg/ml) | % Cytotoxicity |
|---|---|---|---|---|
| SK-MEL-28 | +++ | Inactive | 50 | 0 |
| | | Active | 50 | 30 |
| | | | 10 | 2 |
| | | | 1 | 0 |
| M-2669 | +++ | Active | 50 | 100 |
| | | | 10 | 58 |
| | | | 1 | 2 |
| M-2765 | +++ | Active | 50 | 100 |

TABLE V-continued

Lysis of Tumor Cells by Antibody MG-21 In the Presence of Unheated Human Serum as a Source of Complement

| Target Cells | GD3 Expression | Complement | MG-21 (μg/ml) | % Cytotoxicity |
|---|---|---|---|---|
| H-3021 | — | Active | 10 | 77 |
|  |  |  | 50 | 0 |
| H-2722 | — | Active | 10 | 0 |
|  |  |  | 50 | 1 |
|  |  |  | 10 | 3 |

Cytotoxicity determined in a 4 hr $^{51}$Cr release assay. Cell lines H-3021 and H-2722 are non-melanomas which do not express detectable amounts of the GD3 antigen The results in Table VI demonstrate that by contrast to MG-21, antibodies 96.5 and 48.7 which are specific for melanoma-associated antigens that are strongly expressed, p97 glycoprotein and a proteoglycan, respectively, failed to kill the M-2669 target cell in the presence of complement.

TABLE VI

Complement Mediated Lysis of M-2669 Target Cells by MG-21 Directed Against GD3 Melanoma Antigen as Compared to that of Antibodies Directed Against Melanoma-Associated Protein Antigens

|  | % Complement Dependent Lysis of M-2669 Target Cells | |
|---|---|---|
|  | Antibody Concentration (μg/ml) | |
| Antibody | 50 | 10 |
| MG-21 | 64 | 24 |
| 96.5 | 3 | 2 |
| 48.7 | 1 | 7 |

Antibody 96.5 is specific for p97 a melanoma-associated glycoprotein antigen and antibody 48.7 defines a melanoma-associated proteoglycan antigen, both of which are also strongly expressed on the surface of M-2669 target cells.

In view of the interest in developing therapy for human cancer, the next step was to investigate whether serum from patients with disseminated metastases could serve as an adequate source of complement with antibody MG-21. The results in Table VII demonstrate that the complement dependent cytotoxicity of MG-21 was even slightly greater with serum derived from a patient with Stage IV melanoma than with serum from a normal subject.

TABLE VII

Complement Dependent Lysis of M-2669 Target Cells by Antibody MG-21 in the Presence of Serum from a Normal Human Subject or a Patient with Stage IV Melanoma

| Serum Donor | % Complement Dependent Lysis of M-2669 Cells | | |
|---|---|---|---|
|  | MG-21 Concentration (μg/ml) | | |
|  | 50 | 10 | 1 |
| Normal | 79 | 57 | 0 |
| Stage IV | 83 | 64 | 0 |

TABLE VII-continued

Complement Dependent Lysis of M-2669 Target Cells by Antibody MG-21 in the Presence of Serum from a Normal Human Subject or a Patient with Stage IV Melanoma

| Serum Donor | % Complement Dependent Lysis of M-2669 Cells | | |
|---|---|---|---|
|  | MG-21 Concentration (μg/ml) | | |
|  | 50 | 10 | 1 |
| Melanoma M-7 |  |  |  |

Percentage cytotoxicity statistically different from 0 with p less than or equal to 0.01. No cytotoxicity was observed when antibody or serum alone were assayed.

8. DEPOSIT OF CELL LINES

The cell line MG-21 has been deposited on 2/4/86, with the ATCC, 12301 Parklawn Drive, Rockville, Md. 20852, and has been assigned the following accession numbers:

| Cell Line | Accession Number |
|---|---|
| MG-21 | HB9011 |

The present invention has been described in detail with particular reference to the above embodiments. It will be understood, however, that the present invention is not to be limited in scope by the embodiments disclosed or cell lines deposited which are intended as illustrations of aspects of the invention.

Indeed, various modifications of the invention in addition to those shown and described herein will become apparent to those skilled in the art from the foregoing description. Such modifications are intended to fall within the scope of the appended claims.

What is claimed is:

1. A monoclonal antibody that immunospecifically binds to a GD3 ganglioside antigen expressed by human melanoma cells and which, upon complexing with the GD3 ganglioside antigen, activates serum complement or mediates antibody dependent cellular cytotoxicity in which the monoclonal antibody has the affinity and antigen binding specicity of the monoclonal antibody MG21.

2. A continuous cell line which produces a monoclonal antibody that immunospecifically binds to a GD3 ganglioside antigen expressed by human melanoma cells and which upon complexing with the GD3 ganglioside antigen, activates serum complement or mediates antibody dependent cellular cytotoxicity as deposited with the ATCC and assigned accession number HB9011, in which the monoclonal antibody has the affinity and antigen binding specificity of the monoclonal antibody MG-21.

3. The monoclonal antibody of claim 1 which is modified by the attachment of a signal generating compound.

4. The modified monoclonal antibody of claim 3 in which the signal generating compound is selected from the group consisting of: a radioisotope, a radio-opaque compound, a fluorescent compound, an enzyme, an enzyme substrate, and a dye.

* * * * *